United States Patent
Forsell

(10) Patent No.: US 7,407,481 B2
(45) Date of Patent: *Aug. 5, 2008

(54) IMPOTENCE TREATMENT APPARATUS WITH CONNECTION DEVICE

(76) Inventor: Peter Forsell, Aegeristrasse 86, Zug (CH) CH-8300

( * ) Notice: Subject to any disclaimer, the term of this patent is extended or adjusted under 35 U.S.C. 154(b) by 0 days.

This patent is subject to a terminal disclaimer.

(21) Appl. No.: 10/543,632

(22) PCT Filed: Jan. 31, 2003

(86) PCT No.: PCT/SE03/00174

§ 371 (c)(1),
(2), (4) Date: Jul. 28, 2005

(87) PCT Pub. No.: WO2004/066881

PCT Pub. Date: Aug. 12, 2004

(65) Prior Publication Data

US 2006/0079733 A1 Apr. 13, 2006

(51) Int. Cl.
*A61F 5/00* (2006.01)
*A61B 17/08* (2006.01)
(52) U.S. Cl. ................... 600/38; 606/151; 606/201
(58) Field of Classification Search ............ 600/38–41, 600/29–31; 128/897–899, DIG. 25; 606/151–158, 606/201–203
See application file for complete search history.

(56) References Cited

U.S. PATENT DOCUMENTS

| 5,449,368 | A | 9/1995 | Kuzmak |
| 6,929,625 | B2 * | 8/2005 | Bierman ............... 604/174 |

FOREIGN PATENT DOCUMENTS

| FR | 2 797 181 | 2/2001 |
| WO | 01/47434 | 7/2001 |

OTHER PUBLICATIONS

International Search Report for PCT/SE2003/000174 dated Aug. 22, 2003.

* cited by examiner

*Primary Examiner*—John P Lacyk
(74) *Attorney, Agent, or Firm*—Nixon & Vanderhye P.C.

(57) ABSTRACT

A male sexual impotence treatment apparatus comprises a constriction device implanted in an impotent male patient and engaging the patient's penile tissue. The constriction device includes an elongate adjustable constriction member extending in a loop around the penile tissue or the prolongation thereof. A connection device releasably connects the end portions of the constriction member to each other and an adjustment device adjusts the longitudinal extension of the constriction member in the loop to temporarily constrict the penile tissue or the prolongation thereof to restrict the penile exit blood flow to achieve erection. The connection device includes a female part and a male part fitting into the female part to lock them together. The design of the connection device facilitates laparoscopic surgery for implanting the constriction member.

14 Claims, 2 Drawing Sheets

IMPOTENCE TREATMENT APPARATUS WITH CONNECTION DEVICE

This application is the US national phase of International Application No. PCT/SE2003/000174 filed 31 Jan. 2003, which designated the U.S., the entire content of which is incorporated herein by reference.

The present invention relates to a male sexual impotence treatment apparatus, comprising a constriction device implantable in a male patient, who suffers from sexual impotence, for engaging the patient's penile tissue or the prolongation thereof. The constriction device includes an elongate adjustable constriction member adapted to extend in a loop around the penile tissue or the prolongation thereof, the constriction member having first and second end portions. The apparatus further comprises a connection device for releasably connecting the first and second end portions of the constriction member to each other, and an implantable adjustment device adapted to adjust the longitudinal extension of the constriction member in the loop to temporarily constrict the penile tissue or the prolongation thereof to restrict the penile exit blood flow to achieve erection.

The expression "penile tissue or the prolongation thereof" should be understood to mean the penile tissue extended inside the human body and following the pathway of the blood flow leaving the penis i.e. one or more exit veins from the penis, the corpus cavernosum, crura or the prolongation thereof.

BACKGROUND OF THE INVENTION

Male sexual impotence is a widespread problem. Many different solutions to this problem have been tried. A main solution currently practised and disclosed in for instance U.S. Pat. Nos. 5,437,605 and 4,841,461 is to implant a hydraulic inflatable silicone prosthesis in the cavities of the corpora cavernosa of the patient's penis. In fluid connection with this prosthesis is a reservoir implanted in the scrotum. By manual pumping action the prosthesis is filled with fluid from the reservoir to effect erect penile condition or is emptied of fluid, which returns to the reservoir, to effect flaccid penile condition. However, there are several more or less severe disadvantages of this main solution. Above all, the penis is more or less damaged by the operation and it is practically impossible to reverse the operation. Another disadvantage is that rather strong forces act against this implanted prosthesis resulting in a significant risk of the prosthesis being broken.

Another solution to achieve erection is to restrict the blood flow leaving the penis. For example, U.S. Pat. No. 4,829,990 discloses two hydraulically operated inflatable cuffs wrapped around the respective crura. A disadvantage of such a solution is that it involves complicated surgery. Another example on this solution is given by U.S. Pat. No. 4,828,544, which discloses an artificial fistula system surgically implanted and providing a primary fistula between the femoral artery and the femoral vein and a secondary fistula for leading blood from the primary fistula to the penis. An inflatable balloon engages the primary fistula between the secondary fistula and the vein. The balloon is in fluid connection with a manually compressible reservoir implanted in the scrotum. Again, implantation of this artifical fistula system requires delicate surgery.

Yet another example on the blood flow restriction solution is given by WO 01/54626, which discloses an elongate hydraulically adjustable constriction member adapted to temporarily constrict the penile tissue or the prolongation thereof of a patient's penile tissue to restrict the blood flow leaving the penis to achieve erection.

BRIEF SUMMARY OF THE INVENTION

The object of the present invention is to provide a new convenient apparatus for treating impotence, which is easy to apply on and, if desired, easy to remove from an impotent patient's penile tissue or the prolongation thereof tissue.

This object is obtained by an apparatus of the kind presented initially characterised in that the connection device includes a female part and a male part fitting into the female part to lock them together.

The constriction device may be implanted in the base of the patient's penis or the prolongation thereof and preferably may engage the corpus cavernosum, crura or the prolongation thereof of the penis. However, there are several alternative positions of the constriction device that give more or less satisfactory restriction of the blood flow leaving the penis. Thus, as a first alternative the constriction device may extend around both corpora cavernosa or crura of the penis as a single unit. As a second alternative the constriction device may comprise two elongated constriction members extending around the respective corpora cavernosa or crura. As a third alternative an elongated constriction member of the constriction device may encircle one or more of the penile exit veins. As a fourth alternative the constriction device may comprise several constriction members extending around the respective penile exit veins.

In accordance with a preferred embodiment of the invention, the male part includes a shank and a head on the shank and the female part includes two jaws defining a bore for receiving the head of the male part and a passage narrower than and extending from the bore for receiving the shank of the male part, whereby the male part can be locked to the female part by laterally displacing the head and shank of the male part into the bore and passage, respectively. The jaws are formed with indentations in the bore adjacent the passage, such that the head can be displaced laterally relative to the bore into the indentations, whereby the head is prevented from being displaced out of the bore.

Other embodiments of the invention are also conceivable. For example, the male and female parts may be designed as snap fasteners or male and female pipes, which may or may not be provided with threads.

The constriction member may be non-inflatable and the adjustment device may include a motor for adjusting the non-inflatable constriction member. Alternatively, the constriction member may be a hydraulic constriction member, typically with an inflatable cavity, and the adjustment device may include a pump hydraulically connected to the hydraulic constriction member.

Generally, the adjustment device comprises a powered adjustment device, for example including a motor, preferably an electric motor. The apparatus may comprise an implantable energy-transforming device adapted to transform wireless energy emitted from outside the patient's body into an energy form suited for powering the adjustment device. Such an energy form may be electric energy for powering an electric motor of the adjustment device.

To conveniently adjust the constriction of the penile tissue or the prolongation thereof, the apparatus may comprise a wireless remote control for controlling the adjustment device from outside the patient's body to adjust the constriction device.

The invention also provides a method for laparoscopically implanting in a patient a constriction device of the apparatus as described above. The method comprises insufflating the patient's abdomen, placing at leas two laparoscopic trocars in the abdomen, using a dissecting tool inserted through the laparoscopic trocars, dissecting the region of the penile tissue or the prolongation thereof, introducing a constriction device of the apparatus described above through the trocars, and using tools inserted in the trocars forming a loop of the constriction member of the restriction device around the penile tissue or the prolongation thereof in the dissected region and connecting the male and female parts to each other.

The invention also provides a method for laparoscopically removing a constriction device of the apparatus as described above. The method comprises insufflating the patient's abdomen, placing at least two laparoscopic trocars in the abdomen, and using tools inserted in the trocars releasing the male and female parts of the constriction device from each other and then removing the constriction device from the patient.

BRIEF DESCRIPTION OF THE DRAWINGS

In the enclosed drawings.

DETAILED DESCRIPTION OF THE INVENTION

Figure 1:
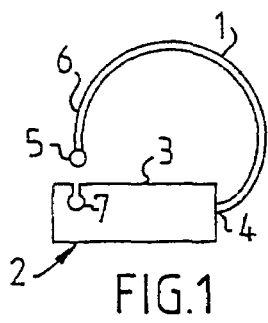
FIG. 1 is a view of the apparatus of the invention with a connection device.

FIG. 1 shows the apparatus of the present invention including a constriction device having an elongated constriction member 1 to be formed into a closed loop around an impotent patient's penile tissue. An adjustment device 2 includes an elongate housing 3 connected to an end portion 4 of the constriction member 1. There is a connection device in the form of a male part 5 on another end portion 6 of the constriction member 1 and a female part 7 formed on the housing 3. (Alternatively, the male part 5 may be provided on the housing 3 and the female part 7 may be formed on the end portion 6.)

Figure 2:
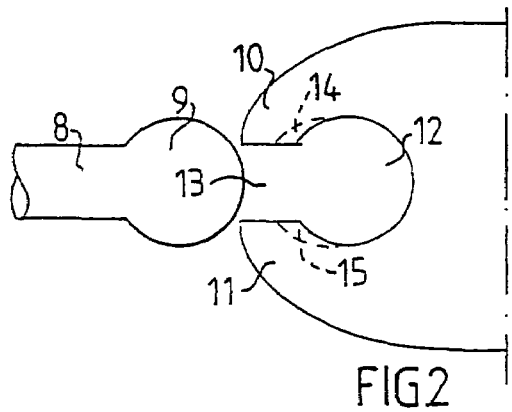
FIG. 2 is a schematic view of the connection device in an unlocked state.
Figure 3:
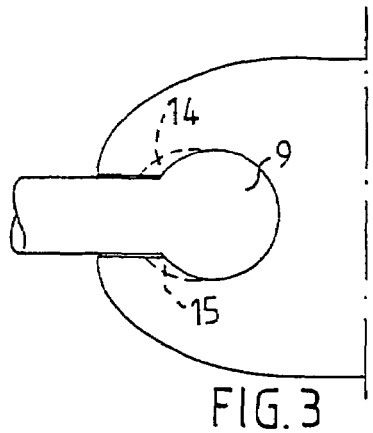
FIG. 3 is a schematic view of the connection device in a pre-locked state.
Figure 4:
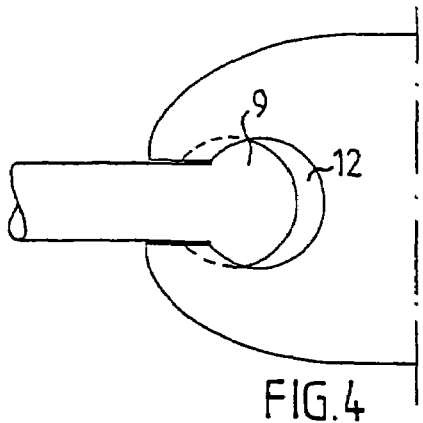
FIG. 4 is a schematic view of the connection device in a final locked state.

With reference to FIGS. 2-4, the male part 5 has a shank 8 and a spherical head 9 on the shank 8 and the female part 7 has two jaws 10,11 defining a circular bore 12 for receiving the head 9 and a passage 13 narrower than and extending from the bore 12 for receiving the shank 8. As appears from FIG. 3 the male part 5 can be pre-locked to the female part 7 by laterally displacing the head 9 and shank 8 into the bore 12 and passage 13, respectively. The jaws 10,11 are formed with spherical segment indentations 14,15 complementary to the spherical head 9. The indentations 14,15 are located in the bore 12 adjacent the passage 13. As appears from FIG. 4 the male part 5 can be finally locked to the female part 7 by displacing the head 9 laterally relative to the bore 12 into the indentations 14,15. The pressure that the penile tissue constantly exerts on the constriction member when the apparatus is implanted ensures that the connection device 5,7 is kept in a locked state.

In case the apparatus should be removed from the patient, the surgeon may conveniently use laparoscopic surgery to introduce a suitable tool into the patient's abdomen to release the head 9 from the jaws 11,11 and displace the head 9 out of the bore 12.

Figure 5:
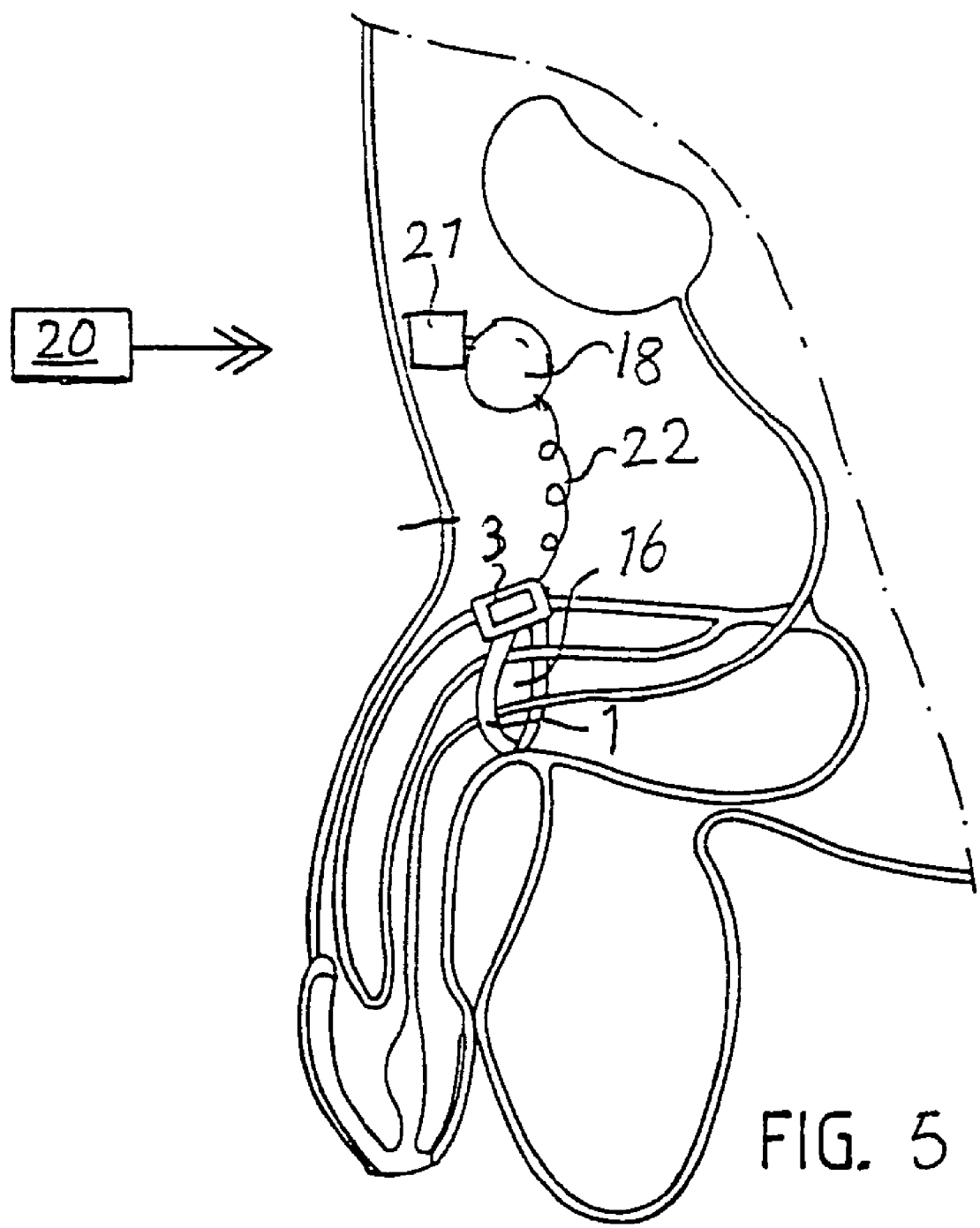
FIG. 5 illustrates the apparatus of the invention implanted in an impotent patient.

FIG. 5 illustrates the constriction device of the embodiment shown in FIGS. 1-4 applied on the penile tissue 16 of an impotent patient. The elongate constriction member 1 and housing 3 of the constriction device extend in a loop around the penile tissue. A rechargeable electric power supply 18 is implanted in the patient to supply electric energy for the operation of the adjustment device 2. When the patient desires to achieve erection, he uses an external remote control 20 to control the adjustment device 2 to adjust the constriction member 1 to constrict the penile tissue, whereby the penile exit blood flow is restricted causing the penis to assume erect condition.

The remote control 20 transmits signals that are received by a combined control and energy-transforming unit 21 subcutaneously implanted in the patient. The unit 21 is electrically connected to the electric power supply 18 and transforms the energy of the signals into an electric current that is used for charging the electric power supply 18. For example, the signals may include electromagnetic waves and the unit 21 may include an electric p-n junction element that transforms the wireless energy into an electric current.

A resilient insulated electric wire 22 connects the power supply 18 and an electric motor of the adjustment device 2 contained in the housing 3. The electric wire 22 extends helically between the power supply 18 and housing 3, in order to permit the electric wire 22 to be temporarily extended when movements of the penile tissue 16 occur, so that the risk of breaking the electric wire 22 is eliminated.

The invention claimed is:

1. A male sexual impotence treatment apparatus, comprising a constriction device implantable in a male patient, who suffers from sexual impotence, for engaging the patient's penile tissue or the prolongation thereof, the constriction device including an elongate adjustable constriction member adapted to extend in a loop around the penile tissue or the prolongation thereof, the constriction member having first and second end portions, a connection device for releasably connecting the first and second end portions of the constriction member to each other, and an implantable adjustment device adapted to adjust the longitudinal extension of the constriction member in the loop to temporarily constrict the penile tissue or the prolongation thereof to restrict the penile exit blood flow to achieve erection, the connection device including a female part and a male part for insertion into the female part, the male part comprising a shank and a spherical head on the end of the shank and the female part comprising two jaws with an open front and two open sides, the jaws defining a semi-spherical bore and a passage narrower than and extending from the bore to the open front of the jaws for removably receiving the spherical head and the shank, respectively, the bore being larger in volume than the spherical head of the male part, the male part being locked to the female part, after the spherical head and shank have been inserted through one of the open sides of the jaws into the bore and passage, respectively, by displacing the spherical head within the semi-spherical bore in the direction of the passage and the shank along the passage away from the bore and towards the open front of the jaws, whereupon the longitudinal extension of the constriction member in the loop can be adjusted to constrict the penile tissue or the prolongation thereof without the male part separating from the female part.

2. An apparatus according to claim 1, wherein the jaws are formed with indentations in the circular bore that are adjacent to the passage and that fit the spherical head of the male part, such that the head can be displaced within the bore into the indentations to lock the male and female parts to each other.

3. An apparatus according to claim 1, wherein the constriction member is non-inflatable.

4. An apparatus according to claim 3, wherein the adjustment device comprises a motor.

5. An apparatus according to claim 1, wherein the constriction member comprises a hydraulic constriction member and the adjustment device comprises a pump hydraulically connected to the hydraulic constriction member.

6. An apparatus according to claim 1, wherein the adjustment device comprises a powered adjustment device and further comprising an implantable energy transforming device adapted to transform wireless energy emitted from outside the patient's body into an energy form suited for powering the adjustment device.

7. An apparatus according to claims 1, further comprising a wireless remote control for controlling the adjustment device to adjust the constriction device.

8. A male sexual impotence treatment apparatus, comprising a constriction device implantable in a male patient, who suffers from sexual impotence, for engaging the patient's penile tissue or the prolongation thereof, the constriction device comprising an elongate adjustable constriction member adapted to extend in a loop around the penile tissue or the prolongation thereof, the constriction member having first and second end portions, a connection device for releasably connecting the first and second end portions of the constriction member to each other, and an implantable adjustment device for adjusting the longitudinal extension of the constriction member in the loop to temporarily constrict the penile tissue or the prolongation thereof to restrict the penile exit blood flow to achieve erection, the connection device including a female part and a male part for insertion into the female part, the male part comprising a shank and a head on the end of the shank and the female part comprises two jaws with an open front and two open sides, the jaws defining a bore and a passage narrower than and extending from the bore to the open front of the jaws for removably receiving the head and the shank, respectively, the bore being larger in volume than the head of the male part, the male part being locked to the female part after the head and shank have been inserted through one of the open sides of the jaws into the bore and passage, respectively, by displacing the head within the bore in the direction of the passage and the shank along the passage away from the bore and towards the open front of the jaws, the jaws being formed with indentations in the bore that are adjacent to the passage and that fit the head of the male part, such that the head can be displaced within the bore into the indentations to lock the male and female parts to each other, whereupon the longitudinal extension of the constriction member in the loop can be adjusted to constrict the penile tissue or the prolongation thereof without the male part separating from the female part.

9. An apparatus according to claim 8, wherein the constriction member is non-inflatable.

10. An apparatus according to claim 9, wherein the adjustment device comprises a motor.

11. An apparatus according to claim 8, wherein the constriction member comprises a hydraulic constriction member and the adjustment device comprises a pump hydraulically connected to the hydraulic constriction member.

12. An apparatus according to claim 8, wherein the adjustment device comprises a powered adjustment device and further comprising an implantable energy transforming device adapted to transform wireless energy emitted from outside the patient's body into an energy form suited for powering the adjustment device.

13. An apparatus according to claim 8, further comprising a wireless remote control for controlling the adjustment device to adjust the constriction device.

14. An apparatus according to claim 8, wherein the head of the male part is spherical and the two jaws of the female part define a semi-spherical bore for receiving the spherical head of the male part.

\* \* \* \* \*